United States Patent [19]
Rao

[11] Patent Number: 5,367,086
[45] Date of Patent: Nov. 22, 1994

[54] PROCESS FOR THE PREPARATION OF TAXOL AND 10-DEACETYLTAXOL

[75] Inventor: Koppaka V. Rao, Gainesville, Fla.

[73] Assignee: University of Florida, Gainesville, Fla.

[21] Appl. No.: 29,078

[22] Filed: Mar. 10, 1993

Related U.S. Application Data

[63] Continuation-in-part of Ser. No. 851,469, Mar. 13, 1992, Pat. No. 5,200,534.

[51] Int. Cl.$^5$ .......................................... C07D 305/14
[52] U.S. Cl. ...................................... 549/510; 549/511
[58] Field of Search ................................. 549/510, 511

[56] References Cited

U.S. PATENT DOCUMENTS

Re. 32,277  6/1993  Denis et al. ...................... 547/510
4,924,011  5/1990  Denis et al. ...................... 549/510

OTHER PUBLICATIONS

Wani, M. C., J. A. Kepler, J. B. Thompson, M. E. Wall, and S. G. Levine (1971) "Plant Antitumor Agents. VI. The Isolation and Structure of Taxol, a Novel Antileukemic and Antitumor Agent From *Taxus brevifolia*" J. Am. Chem. Soc. 93:2325–2327.

Denis, Jean–Noel, and Andrew E. Greene (1988) "A Highly Efficient, Practical Approach to Natural Taxol" J. Am. Chem. Soc. 110:5917–5919.

Senilh, V., S. Blechert, M. Colin, D. Guenard, F. Picot, P. Potier, et P. Varenne (1984) "Mise En Evidence De Nouveaux Analogues Du Taxol Extraits De Taxus Baccata" Journal of Natural Products 47(1):131–137.

*Primary Examiner*—C. Warren Ivy
*Assistant Examiner*—Ba K. Trinh
*Attorney, Agent, or Firm*—Saliwanchik & Saliwanchik

[57] ABSTRACT

Taxol, 10-deacetyltaxol and other taxane derivatives are prepared from naturally occurring taxane-7-xylosides by the oxidative cleavage of the 7-xyloside moieties.

28 Claims, No Drawings

PROCESS FOR THE PREPARATION OF TAXOL AND 10-DEACETYLTAXOL

CROSS-REFERENCE TO A RELATED APPLICATION

This application is a continuation-in-part of application Ser. No. 07/851,469, filed Mar. 13, 1992 now U.S. Pat. No. 5,200,534.

BACKGROUND OF THE INVENTION

1. Field of the Invention

This invention relates to the preparation of taxol and 10-deacetyltaxol by partial synthesis starting from various naturally occurring taxane-7-xylosides.

2. Related Art

Taxol was first isolated in 1971 from the western yew, *Taxus brevifolia* by Wani et al. ([1971] *J. Am. Chem. Soc.* 93:2325), who characterized its structure by chemical and X-ray crystallographic methods.

Taxol is a member of the taxane family of diterpenes having the following structure:

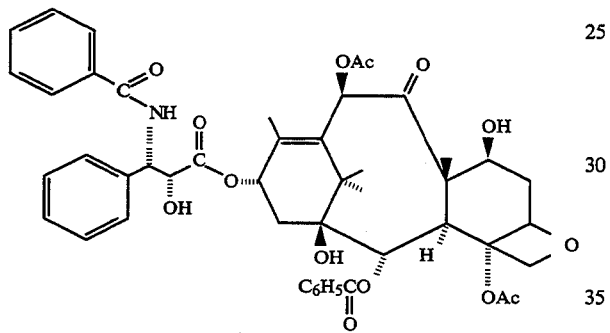

Taxol and various taxane derivatives, including cephalomannine and taxol C, are highly cytotoxic and possess strong in vivo activity in a number of leukemic and tumor systems. In recent studies, taxol has become an exceptionally promising cancer chemotherapeutic agent, and has been approved for use by the Food and Drug Administration (FDA). However, the major problem encountered during the clinical trials conducted for FDA approval was the limited availability of the compound. That problem remains. Various techniques for increasing the supply of taxol are the subject of active research. Strategies being studied include total synthesis, partial synthesis (from readily available taxol precursors), extraction from Taxus needles, cultivation of Taxus plants, identification of simpler drug analog, and cell culture production.

Because of the structural complexity of taxol, partial synthesis is a far more viable approach to providing adequate supplies of taxol than total synthesis. The first successful partial synthesis of taxol was developed by J. N. Denis et al. ([1988] *J. Am. Chem. Soc.* 110:5917; U.S. Pat. No. 4,924,011). The starting material for the partial synthesis, 10-deacetylbaccatin III, can be extracted in relatively high yield from the leaves of *Taxus baccata*. However, thus far, no other naturally occurring taxol precursors have been employed in the partial synthesis of taxol.

Senilh et al. ([1984] *J. Nat. Prod.* 47:131) isolated a number of taxane xylosides from the bark of Taxus baccata. The major xyloside isolated in that study was 10-deacetyltaxol-7-xyloside (0.022%). 10-deacetyltaxol-7-xyloside was also isolated from the bark of *T. brevifolia*, together with taxol-7-xyloside, 10-deacetylcephalomannine-7-xyloside, and 10-deacetyltaxol C-7-xyloside. Among these various compounds, 10-deacetyltaxol-7-xyloside appears to be one of the major components of the bark. Some batches of bark yield 0.1% or more of this compound which is nearly 5 times as much as that reported earlier by Senilh. Thus, it would be desirable to use 10-deacetyltaxol-7-xyloside as a starting material to synthesize taxol. Unfortunately, all previous attempts at converting 10-deacetyltaxol-7-xyloside into taxol have failed. The present invention addresses this need by providing a process for the conversion of 10-deacetyltaxol-7-xyloside and other taxol precursors to taxol.

BRIEF SUMMARY OF THE INVENTION

Surprisingly, through the step of oxidatively cleaving the xyloside moiety of 10-deacetyltaxol-7-xyloside or taxol-7-xyloside with an oxidizing reagent, e.g., sodium periodate, these molecules can be convened into 10-deacetyltaxol and taxol, respectively. Thus, the present invention provides a process for the preparation of a taxane of the formula:

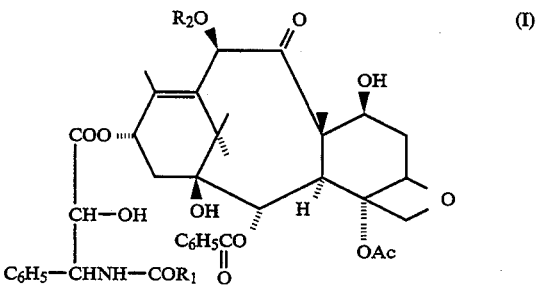

wherein $R_1$ is $Ch_6H_5$, $Ch_5H_{11}$, or

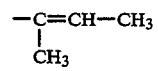

and $R_2$ is hydrogen or acetyl, which comprises the steps of:

(a) reacting an oxidizing reagent with a taxane-7-xyloside of the formula:

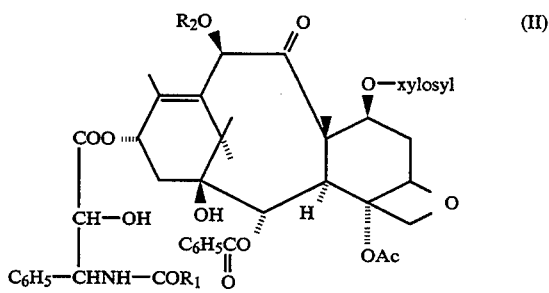

wherein $R_1$ and $R_2$ are as defined, in a reaction-inert solvent at a temperature of from about 20° C. to about 60° C.; and (b) hydrolyzing the glycosyl bond of the products obtained in step (a) with a substituted hydrazine and acetic acid or by acid hydrolysis in a reaction-inert solvent at a temperature of from about 20° C. to about 100° C.

The present invention further encompasses a process for the preparation of a taxane of the formula:

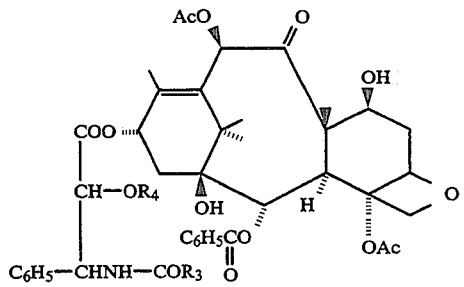

(III)

wherein R₃ is C₆H₅, C₅H₁₁, or

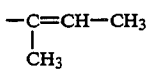

and R₄ is hydrogen or acetyl, which comprises the steps of:

(a) reacting an oxidizing reagent with a taxane-7-xyloside of the formula:

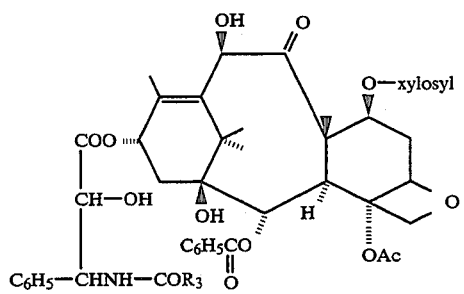

(IV)

wherein R₃ is as defined, in a reaction-inert solvent at a temperature of from about 20° C. to about 60° C.;

(b) reacting the products obtained in step (a) with an acetylating agent in a reaction-inert solvent; and (c) hydrolyzing the glycosyl bond of the acetylated products obtained in step (b) with a substituted hydrazine and acetic acid or by acid hydrolysis in a reaction-inert solvent at a temperature of from about 20° C. to about 100° C.

The present invention also encompasses a process for the preparation of a taxane of the formula (V):

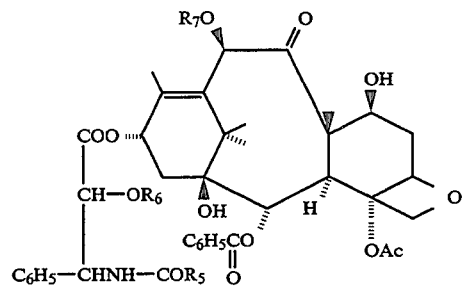

(V)

wherein R₅ is C₆H₅, C₅H₁₁; or

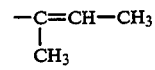

R₆ is hydrogen or an acyl selected from the group consisting of benzoyl, butyryl, carbobenzoxyalanyl, propionyl, succinyl, and trifluoracetyl; and R₇ is an acyl selected from the group consisting of benzoyl, butyryl, carbobenzoxylalanyl, propionyl, succinyl, and trifluoroacetyl, with the proviso that when R6 is an acyl, R₆ and R₇ are the same, which comprise the steps of:

(a) reacting an oxidizing reagent with a taxane-7-xyloside of the formula:

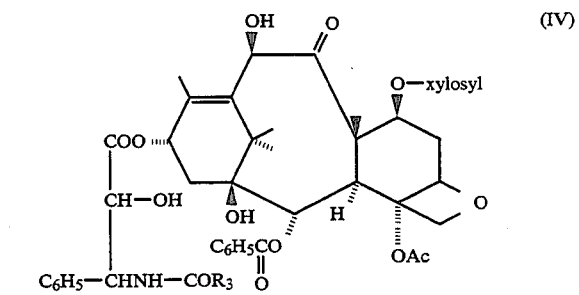

(IV)

wherein R₃ is C₆H₅, C₅H₁₁; or

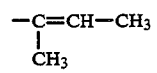

in a reaction-inert solvent at a temperature of from about 0° C. to about 60° C.;

(b) reacting the products obtained in step (a) with an acylating agent in a reaction-inert solvent; and (c) hydrolyzing the glycosyl bond of the acylated products obtained in step (b) with a substituted hydrazine and acetic acid or by acid hydrolysis in a reaction-inert solvent at a temperature of from about 20° C. to about 100° C.

The present invention still further encompasses a process for the preparation of taxol, cephalomannine, or taxol C, comprising the step of deactylating 2'-acetyl group of a compound of formula (III) wherein R₄ is acetyl.

The present invention includes a process for the preparation of 10-acyl-10-deacetyltaxol, 10-acyl-10-deacetylcephalomannine, or 10-acyl-10-deacetyltaxol C, comprising the step of deacylating 2'-acyl group of a compound of formula (III) wherein R₆ is acyl.

The present invention further includes a process of converting 10-deacetyltaxol, 10-deacetylcephalomannine, and 10-deacetyltaxol C into taxol, cephalomannine, and taxol C, respectively.

The present invention also pertains to the discovery that a taxane xyloside, e.g., taxol-7-xyloside, or other taxane derivative comprising a xyloside or other similar sugar moiety, can have unexpected anti-cancer, e.g., antitumor, activity when presented in an oral dosage formulation.

DETAILED DISCLOSURE OF THE INVENTION

The present invention is based in part on the discovery that the xylose moiety of a taxane-7-xyloside can be oxidatively cleaved by the use of an oxidizing reagent, e.g., sodium periodate, followed by treatment with a second reagent, e.g., phenylhydrazine to hydrolyze the glycosyl bond between the xylose and taxane moieties to yield 7-hydroxyl-taxane (taxol) derivatives. The oxidative cleavage reaction sequence employed in the present invention would also be applicable to taxane glycosides other than xylosides. In addition, the present invention can be applied to taxane glycosides having the sugar moiety bound at positions other than the 7 position of the taxane moiety.

Hydrolysis of a taxane xyloside by conventional methods such as acidic treatment on heating is not suitable because the taxane skeleton is susceptible to such treatment. Attempted enzymatic cleavage of the xyloside was also unsuccessful, as reported by Senilh et al., op cit. However, we found that following oxidative cleavage of the sugar moiety as described herein, conventional acid hydrolysis can hydrolyze the glycosyl bond and thereby remove the xylose moiety.

According to one aspect of the present invention, a taxane-7-xyloside of the formula (II) can be convened to a taxane of the formula (I).

In the present oxidative-cleavage process, the oxidation of the xyloside is carried out by reaction of the taxane (II) with at least two-molar equivalent of an oxidizing reagent in a reaction-inert solvent, preferably in a water-miscible solvent. Preferred reagents for the oxidative cleavage step are periodic acid ($HIO_4$) or can be other suitable periodate salts. Suitable periodates for use in the invention are paraperiodic acid, $H_5IO_6$, potassium metaperiodate, sodium metaperiodate, and $NaIO_4$. Most preferably, sodium periodate is used to oxidatively cleave the sugar moiety of the taxane-7-xylosides.

As employed herein, the term "reaction-inert solvent" refers to a solvent which does not significantly interact with reactants, reagents, intermediates, or product in a manner which significantly reduces the yield of the desired products.

Examples of suitable reaction-inert solvents include methanol, ethanol, t-butyl alcohol, dioxane, and acetic acid. Water can be used as a cosolvent. Also, other organic solvents can be used to dissolve water-insoluble compounds.

The cleavage of 1,2-diols by periodate is usually most rapid in the acidity range of pH 1-6. An acidic solvent system such as acetic acid or the presence of an acid is, therefore, preferred. However, alternatively, neutral conditions such as in the presence of excess sodium bicarbonate as a buffer can also be employed. Reaction temperature is not critical, but is preferably in the range of 20° C. to 60° C. Under these conditions, reaction is complete in from about 30 minutes to four hours, providing a dialdehyde product resulting from the cleaved 1,2-diols.

The second step of the present oxidative-cleavage process involves degradation of the dialdehyde product with a reagent suitable to hydrolyze the glycosyl bond between the oxidized sugar moiety and the taxane moiety. This step is carried out by reacting the dialdehyde product after removal of the oxidizing reagent but without further purification, with at least two molar equivalents of the reagent suitable for hydrolyzing the oxidized glycosyl, in the presence of acetic acid in a reaction-inert solvent. Hydrolysis of the glycosyl bond of the taxane-xyloside can be carried out by using a substituted hydrazinc, e.g., phenylhydrazine in the presence of acetic acid. Other suitable hydrazines, for example, alkyl-, aryl-, or acyl-substituted hydrazines and the like can also be used. Alternatively, direct acid treatment with acetic acid or other dilute mineral acids can be employed to carry out hydrolysis of the glycosyl bond. Preferably, 50% acetic acid, dilute (0.01-0.5N) HCl, $H_2SO_4$, HBr, HI, and the like, can be used. The acid hydrolysis step can be carried out under temperature conditions ranging from 20°-100° C., and is preferably carried out between 30°-60° C.

Examples of suitable reaction-inert solvents include methanol, ethanol, t-butyl alcohol, and dioxane. Again, temperature is not critical, but is preferably in the range of 20°-60° C. Under these conditions, the desired products of formula (I) are readily formed in about one hour.

The products of formula (I) are isolated and purified by standard methods well known to those skilled in the art, such as recrystallization or column chromatography.

The compound of formula (II) wherein $R_1$ is $C_6H_5$ and $R_2$ is hydrogen (10-deacetyltaxol-7-xyloside) is converted through the above two-step process, to a product of formula (I) wherein $R_1$ is $C_6H_5$ and $R_2$ is hydrogen (10-deacetyltaxol).

Similarly, the compound of formula (II) wherein $R_1$ is $C_6H_5$ and $R_2$ is acetyl (taxol-7-xyloside) can be converted to a product of formula (I) wherein $R_1$ is $C_6H_5$ and $R_2$ is acetyl (taxol).

In addition, the compound of formula (II) wherein $R_1$ is

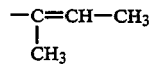

and $R_2$ is hydrogen (10-deacetylcephalomannine-7-xyloside) can be converted to a product of formula (1) wherein $R_1$ is

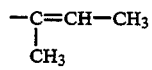

and $R_2$ is hydrogen (10-deacetylcephalomannine).

Moreover, the compound of formula (II) wherein $R_1$ is

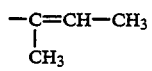

and $R_2$ is acetyl (cephalomannine-7-xyloside) can be converted to a product of formula (I) wherein $R_1$ is

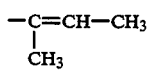

and $R_2$ is acetyl (cephalomannine).

Further, the compound of formula (II), wherein the 3' group is hexanoyl ($R_1=C_5H_{11}$) and $R_2$ is hydrogen (10-deacetyltaxol C-7-xyloside) can be converted to a product of formula (I) wherein $R_1$ is $C_5H_{11}$ and $R_2$ is hydrogen (10-deacetyltaxol C).

Still further, the compound of formula (II) wherein $R_1$ is $C_5H_{11}$ and $R_2$ is acetyl (taxol C-7-xyloside) can be converted to a product of formula (I) wherein $R_1$ is $C_5H_{11}$ and $R_2$ is acetyl (taxol C).

In another aspect of this invention, 10-deacetyltaxol, 10-deacetylcephalomannine, and 10-deacetyltaxol C are then acetylated at the 10-position, producing the desired taxol, cephalomannine, and taxol C, respectively. This acetylation method involves the steps of (1) selective protection of the 7- and 2'-hydroxyl groups, (2) acetylation, and (3) deprotection.

Acetylation can be carried out by reacting the products with a suitable acetylating agent such as excess acetyl chloride or acetyl anhydride. The acylation reaction is usually conducted in a reaction-inert solvent. Preferably, acetylation is conducted in the presence of a tertiary amine, at a temperature in the range from 0° C. to 100° C. Reaction-inert solvents which can be used in this acylation are: chlorinated hydrocarbons, such as chloroform and dichloromethane; ethers, such as diethyl ether and tetrahydrofuran; low molecular weight esters, such as ethyl acetate and butyl acetate; low molecular weight aliphatic ketones, such as acetone and methyl ethyl ketone; tertiary amides, such as N,N-dimethyl formamide and N-methylpyrridone; acetonitrile; and mixtures thereof. The typical tertiary amines which can be used are triethylamine, tributylamine, diisopropylethylamine, pyridine, and 4-dimethylaminopyridine.

Prior to the acetylation step, the 10-deacetyltaxanes are treated with a suitable protecting agent to protect its 7- and 2'-hydroxyl position. Suitable protecting groups include chloroacetate, trichloroacetate, trichloroethyl carbonate, and triethylsilyl ether. A preferred protection method involves the use of chloroacetic anhydride in a reaction inert solvent, preferably in the presence of a tertiary amine. The reaction-inert solvents and the tertiary amines usable in this step are not significantly different from those described earlier for the acetylation step.

Once acetylation has been completed, the deprotection of the 7- and 2'-hydroxyl protecting groups is carried out by treating with a suitable deprotecting agent. When the protecting group is chloroacetate, the deprotection procedure employs thiourea. Other deprotecting agents that can be used include aminoethanethiol, ethylene diamine, and o-phenylene diamine.

Following the protection, acetylation, and deprotection steps, taxol, cephalomannine, and taxol C can be derived from 10-deacetyltaxol, 10-deacetylcephalomannine, and 10-deacetyltaxol C, respectively.

According to a further aspect of the present invention, the compounds of formula (IV) are first subjected to the oxidative cleavage step and the reaction products are acetylated without further purification. This acetylation is carried out in the same manner as that described for the acetylation of 10-deacetyltaxol, 10-deacetylcephalomannine, and 10-deacetyltaxol C.

The acetylation products are then exposed to the conditions employed for the second step of the present oxidative-cleavage process, preferably, treatment with phenylhydrazine and acetic acid. Prolonged treatment tends to cause the hydrolysis of the initially-formed 2'-acetyl group. Products thus formed are compounds of formula (III) wherein $R_4$ can be hydrogen or acetyl.

When the starting material is 10-deacetyltaxol-7-xyloside, the resulting products can be 2'-acetyltaxol and taxol. Each product can readily be purified, e.g., by recrystallization or column chromatography.

The compound of formula (III) wherein $R_4$ is acetyl may be selectively hydrolyzed at the 2'-acetyl position, thus providing a compound of formula (III) wherein $R_4$ is hydrogen. The hydrolysis can be carried out in the presence of a weak base in a reaction-inert solvent, e.g., lower alcohol. Suitable base agents include sodium bicarbonate, potassium bicarbonate, dimethylamine, and diethylamine. A particularly preferred solvent is methanol. Reaction is normally conducted at ambient temperature.

More conveniently, the mixture of the acetylated products, without separation and purification, are exposed to the afore-described selective hydrolysis conditions, thus yielding only the compound of formula (III) wherein $R_4$ is hydrogen.

In a similar manner to the conversion of compounds (IV) to compounds (III), the compounds (IV) are first subjected to the oxidative cleavage step and the reaction products are acylated without purification. Suitable acylating agents which can be used include succinic anhydride, propionic anhydride, butyric anhydride, benzoyl chloride, carbobenzoxy alanyl chloride, and trifluoroacetic anhydride. This acylation is carried out under substantially the same conditions as those described for the above-indicated acetylations.

The acylation products are then exposed to the conditions employed for the second step of the present oxidative-cleavage process. Products thus formed are compounds of formula (V).

When the starting material is 10-deacetyltaxol-7-xyloside, the resulting product can be 2',10-diacyl 10-deacetyl taxol and 10-acyl-10-deacetyl taxol. The diacyltaxol may be hydrolyzed with a base in substantially the same manner as that used for the selective deacetylation of the compounds (III), providing 10-acyl-10-deacetyltaxol.

The taxane 7-xylosides of formula (II) and (IV), required as starting materials for the invention, are available by the isolation from the taxus species according to the methods well known in the art (see, for example, the references to 10-deacetyltaxol-7-xyloside cited above).

The process of this invention allows the preparation of taxol in a highly efficient manner from various taxane-7-xylosides which have not been hitherto utilized.

In addition, another aspect of the invention is to use the taxane compounds comprising a glycoside, e.g., a taxane xyloside, in an oral dosage formulation for anticancer indications similar to taxol, e.g., for its antitumor activity. Therapeutic application of the glycosidic compounds and compositions comprising those compounds can be contemplated to be accomplished by any suitable therapeutic method and technique presently or prospectively known to those skilled in the art. For example, as stated, the xyloside compounds of the invention have use as starting materials or intermediates for the preparation of the useful anti-cancer compound taxol. When presented as a glycosidic compound, a taxane can be readily absorbed by the digestive tract, whereas a taxane without a sugar moiety is relatively poorly absorbed. The enhanced absorption characteristics of the taxane glycoside can allow the active ingredient to be administered in an oral dosage formulation. The active ingredient can be the taxane glycoside, itself, or a taxane compound wherein the glycosidic moiety has been hydrolyzed metabolically following absorption.

The dosage administration to a host in the above indications will be dependent upon the identity of the cancer, the type of host involved, its age, weight, health, kind of concurrent treatment, if any, frequency of treatment, and therapeutic ratio.

The glycoside compounds of the subject invention can be formulated according to known methods for preparing pharmaceutically useful compositions. Formulations for oral dosage compositions are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition. Suitable carriers can be non-toxic carriers or diluents.

The present invention is illustrated by the following examples. The examples illustrate procedures, including the best mode, for practicing the invention. However, it should be understood that the invention is not limited to the specific details of these examples. All percentages are by weight and all solvent mixture proportions are by volume, unless otherwise specified.

Example 1—10-Deacetyltaxol

To a solution of 0.5 g of 10-deacetyltaxol-7-xyloside in 25 ml of methanol/chloroform (4:1) was added 0.3 g of sodium periodate and 2 ml of 1N sulfuric acid. Stirring was continued for about 3 hours at room temperature. The reaction mixture was diluted with 100 ml of water and the organic phase was extracted with 50 ml of chloroform (×3). The organic extracts were concentrated to dryness, yielding 0.5 g of a product. The product (0.5 g) was dissolved in 10 ml of methanol and 5 ml of 50% aqueous acetic acid. The resulting solution was mixed with 0.2 ml of phenylhydrazine. The mixture was heated at 50°–60° C. for 1 hour. After cooling, the reaction mixture was diluted with 20 ml of water and the organic phase was extracted with 20 ml of chloroform (×2). The combined chloroform extract was concentrated to dryness under reduced pressure. The resulting residue was chromatographed on 10 g of silica gel using chloroform/ligroin (2:1) as eluant. The eluant was changed to chloroform, 2–5% acetone in chloroform, and finally, 2–5% methanol in chloroform.

The appropriate fractions were combined and concentrated under reduced pressure. The residue was recrystallized from chloroform to give 0.2 g of the title compound, m.p. 192°–196° C.

The spectroscopic characteristics of the product are identical in all respects with an authentic sample (as reported in McLaughlin, J. L. et al. [1981] *J. Nat. Prod.* 44:312).

Example 2—10-Deacetylcephalomannine

In the manner of the procedure of Example 1, 0.5 g of 10-deacetylcephalomannine-7-xyloside was oxidatively cleaved to give 0.2 g of the title compound, identical in all respects with an authentic sample (Miller, R. W. et al. [1981] *J. Org. Chem.* 46).

Example 3—10-Deacetyltaxol C

In the manner of Example 1, 0.5 g of 10-deacetyltaxol C-7-xyloside was oxidatively cleaved to give approximately 0.2 g of the title compound, identical in all respects with an authentic sample (Senilh et al., supra).

Example 4—Taxol

In the manner of the procedure of Example 1, 0.5 g of taxol-7-xyloside was oxidatively cleaved. The product, after treatment with phenylhydrazine, was taken up in 25% acetonitrile in water and applied to a column of 10 g of C-18 reverse phase silica. The column was eluted with a gradient of acetonitrile in water (30, 35, 40, 45, and 50%).

The appropriate factors were combined and concentrated under reduced pressure. The residue was recrystallized from acetonitrile/water to give 0.2 g of the title compound, identical in all respects with an authentic sample (Wani et al., op. cit.).

Example 5—Cephalomannine

In the manner of the procedure of Example 1 as modified in Example 3, 0.5 g of cephalomannine-7-xyloside was oxidatively cleaved to give 0.2 g of the title compound, identical in all respects with an authentic sample (Miller, R. W., op. cit.).

Example 6—Taxol C

In the manner of the procedure of Example 1, as modified in Example 4, approximately 0.5 g of taxol C-7-xyloside was oxidatively cleaved to give about 0.2 g of the title compound, identical in all respects with an authentic sample (Miller, R. W., op. cit.).

Example 7—Taxol

To a solution of 1 g of 10-deacetyltaxol-7-xyloside in 50 ml of methanol/chloroform (4:1) was added 0.6 g of sodium periodate and 4 ml of 1N sulfuric acid. Stirring was continued for about 3 hours at room temperature. The reaction mixture was diluted with 50 ml of water and the organic phase was extracted with 50 ml of chloroform (×2). The organic extracts were concentrated to dryness, yielding a colorless solid (1.0 g).

The solid (1.0 g) was dissolved in 5 ml of acetic anhydride and 1 ml of pyridine. The solution was heated at 100° C. for about 30 minutes. After cooling, the mixture was diluted with 50 ml of water and 1 g of a colorless solid was collected by filtration. The resulting solid (1 g) was dissolved in 20 ml of methanol/chloroform (4:1). To the solution was added 3 ml of acetic acid and 0.5 ml of phenylhydrazine. The mixture was heated at 50°–60° C. for about 3 hours. After cooling, the reaction mixture was diluted with 20 ml of water and the organic phase was extracted with 20 ml of chloroform (×2). The combined chloroform extract was concentrated to dryness under reduced pressure. The resulting residue was chromatographed on a reverse phase $C_{-8}$ column using 25% acetonitrile in water as eluant. A gradient of acetonitrile in water (30, 35, 40, 45, and 50% acetonitrile) was successively used as eluant. The appropriate fractions were combined and concentrated under reduced pressure. The earlier fractions gave 0.1 g of the title compound. The later fractions gave 0.5 g of 2'-acetyltaxol, which was recrystallized from acetone/ligroin to afford 0.4 g of a colorless crystalline solid. The product thus obtained was identical in all respects with an authentic sample (Mellado et al. [1984] *Biochem. Biophys. Res. Commun.* 124:329).

Example 8—10-Succinyl-10-Deacetyltaxol

In the manner of the procedure of Example 1, 0.5 g of 10-deacetyltaxol-7-xyloside was oxidatively cleaved. The oxidation product was extracted with chloroform, concentrated, and dissolved in 2 ml of pyridine. To the pyridine solution was added 1 g of succinic anhydride. The mixture was heated at 100° C. for 1 hour. After the reaction was complete (monitored by tlc), the cooled mixture was diluted with water. Upon standing for 30 minutes, the mixture was acidified and extracted with chloroform (×2). The chloroform extracts were washed with aqueous sodium bicarbonate solution and concentrated to dryness under reduced pressure.

The resulting product was dissolved in 20 ml of methanol. To the solution was added 3 ml of acetic acid and 0.3 ml of phenylhydrazine. The mixture was heated at 70°–90° C. for about 2 hours. When the reaction was complete, the reaction mixture was diluted with 30 ml of water and the organic phase was extracted with chloroform (×2). The combined chloroform extract was concentrated to dryness under reduced pressure. The residual solid was chromatographed on a silica gel column using 2:1 chloroform/ligroin as eluant The eluant was successively changed to chloroform, 2–5% acetone in chloroform, and 2–5% methanol in chloroform. The product recovered was 2',10-disuccinyl-10-deacetyl-taxol. The disuccinate (0.2 g) was dissolved in 10 ml of methanol and treated with an equal volume of dimethylamine in methanol (about 0.2–0.8%). The reaction was monitored by tlc or HPLC until hydrolysis was complete. The reaction mixture was acidified by addition of a few drops of acetic acid and concentrated to dryness under reduced pressure. The resulting solid was recrystallized from acetone/ligroin to yield 0.1 g of the title compound.

Example 9—Oxidative Cleavage of a Taxane-7-Xyloside with Lead Tetraacetate 10-deacetyltaxol-7-xyloside (0.5 g) is dissolved in acetic acid (20 ml) and stirred with lead tetraacetate (0.3 g). After 1 hour, when tlc showed reaction to be complete, a solution of aqueous sodium bisulfite is added to decompose the excess reagent and the mixture is diluted with water (100 ml). Extraction with chloroform (2×) and concentration of the solvent gave the oxidation product, identical with the product obtained using a periodate for the oxidative cleavage step.

Preparation 1—Taxol From 10-Deacetyltaxol

To a solution of 0.5 g of 10-deacetyltaxol in 2 ml pyridine was added 0.5 g of chloroacetic anhydride at room temperature for 1 hour. The reaction mixture was diluted with water and the resulting solid was filtered. This solid was chromatographed on 10 g of silica gel using chloroform/acetone (2–5%) as eluant. The appropriate fractions were combined and concentrated under reduced pressure to give a solid, which was recrystallized from acetone/hexane. The resulting product (0.5 g) was heated in a mixture of 2 mil of acetic anhydride and 1 ml of pyridine at 100° C. for 30 minutes.

To a solution of the product in 10 ml of ethanol was added 0.2 g of thiourea and 0.1 g of sodium bicarbonate. The resulting mixture was stirred at room temperature for 1 hour and diluted with water. The solid precipitated was collected by filtration and then recrystallized from acetone/ligroin to give 0.3 g of taxol, identical in all respects with an authentic sample.

Preparation 2—Taxol From 2'-Acetyltaxol

A solution of 0.2 g of 2'-acetyltaxol in 10 ml of methanol was treated with aqueous dimethylamine to make a 0.2% solution of dimethylamine. The reaction mixture was monitored by tlc until the hydrolysis was nearly complete. The reaction mixture was then concentrated to dryness under reduced pressure and the solid crystallized from acetone/ligroin to yield 0.12 g of a colorless crystalline solid, identical in all respects with taxol.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. A process for the preparation of a taxane of the formula

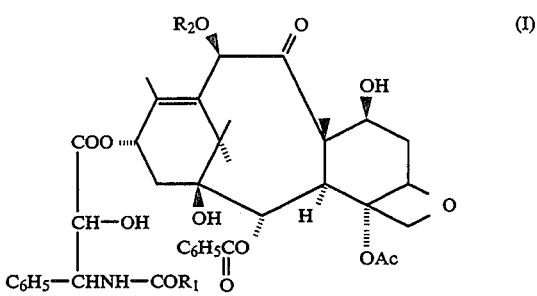

wherein $R_1$ is $C_6H_5$, $C_5H_{11}$, or

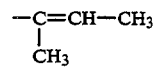

and $R_2$ is hydrogen or acetyl, said process comprising the steps of:

(a) reacting an oxidizing reagent selected from the group consisting of periodate and lead tetraacetate with a taxane 7-xyloside of the formula:

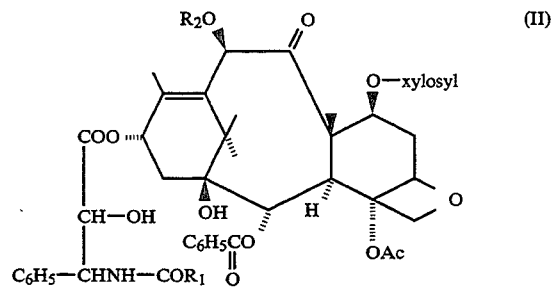

wherein $R_1$ and $R_2$ are as defined, in a reaction-inert solvent at a temperature of from about 20° C. to about 60° C.; and (b) hydrolyzing the glycosyl bond of the product obtained in step (a) with a substituted hydrazine, wherein said substituted hydrazine is selected from the group consisting of an alkyl hydrazine, acyl hydrazine, and aryl hydrazine, and acetic acid or by acid hydrolysis in a reaction-inert solvent at a temperature of from about 20° C. to about 100° C.

2. The process according to claim 1, wherein the oxidizing reagent used in step (a) is a periodate.

3. The process, according to claim 2, wherein the periodate used in step (a) is sodium periodate.

4. The process, according to claim 1, wherein the oxidizing reagent used in step (a) is lead tetraacetate.

5. The process according to claim 1, wherein step (a) is carried out at room temperature.

6. The process, according to claim 1, wherein the hydrolysis step of step (b) is carried out by reacting the product of step (a) with a substituted hydrazine and acetic acid.

7. The process, according to claim 6, wherein the substituted hydrazine is phenylhydrazine.

8. The process, according to claim 1, wherein the hydrolysis of step (b) is carried out by acid hydrolysis.

9. The process, according to claim 8, wherein said acid hydrolysis is carried out by reacting the product of step (a) with 50% acetic acid.

10. The process, according to claim 8, wherein said acid hydrolysis is carried out under conditions of heat.

11. The process, according to claim 10, wherein said heating conditions are a temperature of at least 30° C.

12. The process according to claim 1, further comprising the step of acetylating the compound of formula (I) wherein $R_2$ is hydrogen to produce the compound of formula (I) wherein $R_2$ is acetyl.

13. The process according to claim 12, wherein prior to the step of acetylation the 7- and 2'-hydroxyls of the compound are protected and after the acetylation the 7- and 2'-hydroxyl are deprotected.

14. The process according to claim 13, wherein the acetylation is carried out by contacting the compound with acetic anhydride in the presence of pyridine at a temperature of about 0° C. to about 100° C.

15. A process for the preparation of a taxane of the formula

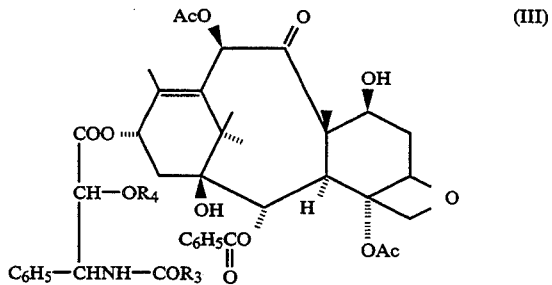

wherein $R_3$ is $C_6H_5$, $C_5H_{11}$, or

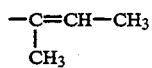

and $R_4$ is hydrogen or acetyl, said process comprising the steps of:

(a) reacting an oxidizing reagent selected from the group consisting of periodate and lead tetraacetate with a taxane-7-xyloside of the formula:

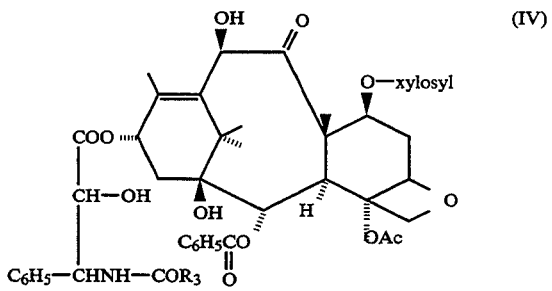

wherein $R_3$ is a defined, in a reaction-inert solvent at a temperature of from about 20° C. to about 60° C.;

(b) reacting the product obtained in step (a) with an acetylating agent in a reaction-inert solvent; and (c) hydrolyzing the glycosyl bond of the acetylated products obtained in step (b) with a substituted hydrazine, said substituted hydrazine selected from the group consisting of alkyl hydrazine, acyl hydrazine, and aryl hydrazine and acetic acid or by acid hydrolysis in a reaction-inert solvent at a temperature of from about 20° C. to about 100° C.

16. The process according to claim 15, wherein the oxidizing reagent used in step (a) is a periodate.

17. The process, according to claim 16, wherein said periodate is sodium periodate.

18. The process, according to claim 15, wherein said oxidizing reagent is lead tetraacetate.

19. The process according to claim 15, wherein step (a) is carried out at room temperature.

20. The process according to claim 15, wherein the acetylating agent is acetic anhydride.

21. The process according to claim 20, wherein the reaction-inert solvent used in step (b) is pyridine.

22. The process according to claim 15, wherein step (b) is carried out at about 0° C. to about 100° C.

23. The process according to claim 15, further comprising the step of deacetylating the compound of formula (III) wherein $R_4$ is acetyl to produce the compound of formula (III) wherein $R_4$ is hydrogen.

24. The process according to claim 23, wherein the deacetylation is carried out by contracting the compound of formula (III) wherein $R_4$ is acetyl with dimethylamine in methanol.

25. A process for the preparation of a taxane of the formula:

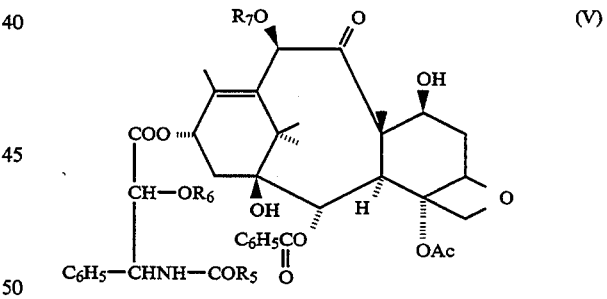

wherein $R_5$ is $C_6H_5$, $C_5H_{11}$; or

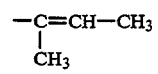

$R_6$ is hydrogen or an acyl selected from the group consisting of benzoyl, butyryl, carbobenzoxyalanyl, propionyl, succinyl, and trifluoroacetyl; and $R_7$ is an acyl selected from the group consisting of benzoyl, butyryl, carbobenzoxylalanyl, propionyl, succinyl, and trifluoroacetyl, with the proviso that when $R_6$ is an acyl, $R_6$ and $R_7$ are the same, said process comprising the steps of:

(a) reacting an oxidizing reagent selected from the group consisting of a periodate and lead tetraacetate with a taxane-7-xyloside of the formula:

(IV)

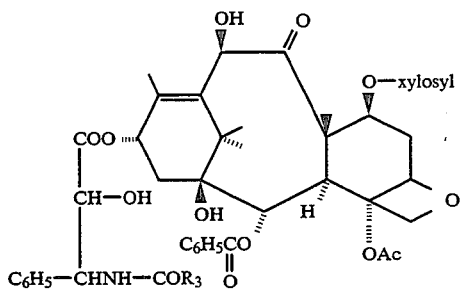

wherein $R_5$ is $C_6H_5$, $C_5H_{11}$; or

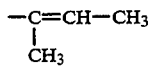

in a reaction-inert solvent at a temperature of from about 0° C. to about 60° C.;

(b) reacting the product obtained in step (a) with an acylating agent in a reaction-inert solvent; and (c) hydrolyzing the glycosyl bond of the acylated products obtained in step (b) with a substituted hydrazine, said substituted hydrazine selected from the group consisting of alkyl hydrazine, acyl hydrazine, and aryl hydrazine, and acetic acid or by acid hydrolysis in a reaction-inert solvent at a temperature of from about 20° C. to about 100° C.

26. The process according to claim 25, further comprising the step of deacylating the compound of formula (V) wherein $R_6$ is an acyl to produce the compound of formula (V) wherein $R_6$ is hydrogen.

27. The process according to claim 26, wherein the deacylation is carried out by contracting the compound of formula (V) wherein $R_6$ is acyl with dimethylamine in methanol.

28. The process according to claim 25, wherein $R_7$ is succinyl.

* * * * *

UNITED STATES PATENT AND TRADEMARK OFFICE
CERTIFICATE OF CORRECTION

PATENT NO. : 5,367,086
DATED : November 22, 1994
INVENTOR(S) : Koppaka V. Rao

It is certified that error appears in the above-indentified patent and that said Letters Patent is hereby corrected as shown below:

Column 2, line 39: Delete "$R_1$ is $Ch_6H_5$, $Ch_5H_{11}$," and insert --$R_1$ is $C_6H_5$, $C_5H_{11}$--.

Column 5, line 22: Delete "convened" and insert --converted--.

Column 9, line 4: Delete "desert'bed" and insert --described--.

Column 10, line 48: Delete "phase C, -8" and insert --phase C-8--.

Column 14, line 59: Delete "trifluoroacetyl;" and insert --trifluoracetyl;--.

Signed and Sealed this

Seventh Day of March, 1995

Attest:

BRUCE LEHMAN

*Attesting Officer*   *Commissioner of Patents and Trademarks*